(12) United States Patent
Guan et al.

(10) Patent No.: US 8,030,540 B2
(45) Date of Patent: Oct. 4, 2011

(54) TRANSGENIC CORN HAVING ENHANCED NUTRITIONAL QUALITIES

(75) Inventors: Hanping Guan, Ames, IA (US); Deborah Wetterberg, Demoines, IA (US); Angela L. McKean, Cary, NC (US); Peter L. Keeling, Ames, IA (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 10/907,936

(22) Filed: Apr. 21, 2005

(65) Prior Publication Data

US 2005/0241020 A1    Oct. 27, 2005

Related U.S. Application Data

(60) Provisional application No. 60/564,030, filed on Apr. 21, 2004.

(51) Int. Cl.
| | |
|---|---|
| C12N 15/82 | (2006.01) |
| C12N 15/63 | (2006.01) |
| C12N 15/31 | (2006.01) |
| A01H 5/10 | (2006.01) |
| A01H 5/00 | (2006.01) |
| A01H 3/00 | (2006.01) |

(52) U.S. Cl. ........ 800/281; 800/287; 800/288; 800/295; 800/300.1; 435/320.1; 435/468; 435/412; 536/23.1; 536/23.7; 536/23.2

(58) Field of Classification Search .................. None
See application file for complete search history.

(56) References Cited

U.S. PATENT DOCUMENTS

| | | | |
|---|---|---|---|
| 5,349,123 A | 9/1994 | Shewmaker et al. | 800/284 |
| 5,498,830 A | 3/1996 | Barry et al. | 800/281 |
| 5,498,831 A | 3/1996 | Burgess et al. | 800/284 |
| 5,608,149 A | 3/1997 | Barry et al. | 800/284 |
| 5,773,693 A | 6/1998 | Burgess et al. | 800/284 |
| 5,792,920 A | 8/1998 | Bridges et al. | 800/284 |
| 5,969,214 A | 10/1999 | Stalker et al. | 800/284 |
| 6,232,529 B1 | 5/2001 | Singletary et al. | 800/281 |
| 6,483,011 B1 | 11/2002 | Stemmer et al. | 800/284 |
| 6,486,383 B1 | 11/2002 | Burrell et al. | 800/284 |
| 6,538,178 B1 | 3/2003 | Kishore | 800/284 |
| 6,538,179 B1 | 3/2003 | Barry et al. | 800/284 |
| 6,538,181 B1 | 3/2003 | Stalker et al. | 800/284 |
| 2003/0233675 A1 * | 12/2003 | Cao et al. | 800/279 |

FOREIGN PATENT DOCUMENTS

| | | |
|---|---|---|
| WO | WO 93/09237 | 5/1993 |
| WO | WO 92/24292 | 10/1994 |
| WO | WO 98/10082 | 3/1998 |
| WO | WO 98/22601 | 5/1998 |
| WO | WO 98/44780 | 10/1998 |
| WO | WO 9844780 | * 10/1998 |
| WO | WO 99/07841 | 2/1999 |
| WO | WO 99/58698 | 11/1999 |

OTHER PUBLICATIONS

Sweetlove et al., "Characterization of transgenic potato (*Solanum tuberosum*) tubers with increased ADPglucose pyrophosphorylase," Biochem. J., 1990, 487-492, vol. 320.
Meyer et al., "Cloning, Expression, and Sequence of an Allosteric Mutant ADPglucose Pyrophosphorylase from *Escherichia coli* B," Arch Biochem, Apr. 1993, 64-71, 302(1).
Govons et al., "Biosynthesis of Bacterial Glycogen—XI: Kinetic Characterization of an Altered Adenosine.," The Journal of Biological Chemistry, Mar. 10, 1973, 1731-1740, 248(5).
Sweetlove et al., "Starch metabolism in tubers of transgenic potato (*Solanum tuberosum*) with increased ADPglucose pyrophosphorylase" Biochem. J., 1996, 493-498, 320.
Stark et al., "Regulation of the Amount of Starch in Plant Tissues by ADP Glucose Pyrophosphorylase" Science, Oct. 9, 1992, 287-292, 258.

* cited by examiner

*Primary Examiner* — Brent Page
(74) *Attorney, Agent, or Firm* — Connolly Bove Lodge & Hutz LLP

(57) ABSTRACT

The invention provides transgenic corn seed, which expresses a gene encoding a double mutant of the *E. coli* glgC gene in endosperm plastids, wherein the mutant protein has a proline to aspartic acid substitution at amino acid 295 and a glutamic acid to lysine substitution at amino acid 296. The transgenic corn seed of the invention is characterized by enhanced levels of a number of amino acids and oil, when compared to isogenic corn seed, which does not express the transgene in an endosperm plastid. However, the amount of starch in the transgenic corn seed of the invention is decreased or unchanged when compared to the amount of starch in the isogenic control corn seed.

31 Claims, 13 Drawing Sheets

**Wild-type *E. coli* ADP-glucose pyrophosphorylase (GlgC) amino acid sequence:**

mvslekndhlmlarqlplksvalilaggrgtrlkdltnkrakpavhfggkfriidfalsncinsgirrmgvitqyqshtlvqhiq
rgwsffneemnefvdllpaqqrmkgenwyrgtadavtqnldiirrykaeyvvilagdhiykqdysrmlidhvekgarctv
acmpvpieeasafgvmavdendkiiefvekpanppsmpndpskslasmgiyvfdadylyelleeddrdensshdfgkd
lipkiteaglayahpfplscvqsdpdaepywrdvgtleaywkanldlasvvpeldmydrnwpirtyneslppakfvqdrs
gshgmtlnslvsggcvisgsvvvqsvlfsrvrvnsfcnidsavllpevwvgrscrlrrcvidracvipegmvigenaeedarr
fyrseegivlvtremlrklghkqer (SEQ ID NO:1)

Figure 1

**Wild-type *E. coli* ADP-glucose pyrophosphorylase (*glgC*) nucleotide sequence:**

atggttagtttagagaagaacgatcacttaatgttggcgcgccagctgccattgaaatctgttgccctgatactggcgggaggacg
tggtacccgcctgaaggatttaaccaataagcgagcaaaaccggccgtacacttcggcggtaagttccgcattatcgactttgcg
ctgtctaactgcatcaactccgggatccgtcgtatgggcgtgatcacccagtaccagtcccacactctggtgcagcacattcagc
gcggctggtcattcttcaatgaagaaatgaacgagtttgtcgatctgctgccagcacagcagagaatgaaaggggaaaactggt
atcgcggcaccgcagatgcggtcacccaaaacctcgacattatccgccgttataaagcggaatacgtggtgatcctggcgggc
gaccatatctacaagcaagactactcgcgtatgcttatcgatcacgtcgaaaaaggcgcacgttgcaccgttgcttgtatgccagt
accgattgaagaagcctccgcatttggcgttatggcggttgatgagaacgataaaattatcgaattcgttgaaaaacctgctaacc
cgccgtcaatgccgaacgatccgagcaaatctctggcgagtatgggtatctacgtctttgacgccgactatctgtatgaactgctg
gaagaagacgatcgcgatgagaactccagccacgactttggcaaagatttgattcccaagatcaccgaagccggtctggcctat
gcgcacccgttcccgctctcttgcgtacaatccgacccggatgccgagccgtactggcgcgatgtgggtacgctggaagcttac
tggaaagcgaacctcgatctggcctctgtggtgccggaactggatatgtacgatcgcaattggccaattcgcacctacaatgaat
cattaccgccagcgaaattcgtgcaggatcgctccggtagccacgggatgacccttaactcactggtttccggcggttgtgtgat
ctccggttcggtggtggtgcagtccgttctgttctcgcgcgttcgcgtgaattcattctgcaacattgattccgccgtattgttaccgg
aagtatgggtaggtcgctcgtgccgtctgcgccgctgcgtcatcgatcgtgcttgtgttattccggaaggcatggtgattggtgaa
aacgcagaggaagatgcacgtcgtttctatcgttcagaagaaggcatcgtgctggtaacgcgcgaaatgctacggaagttaggg
cataaacaggagcgataa (SEQ ID NO:2)

Figure 2

**GlgC3 Mutant *E. coli* ADP-glucose pyrophosphorylase (P295D, E296K) amino acid sequence** mvslekndhlmlarqlplksvalilaggrgtrlkdltnkrakpavhfggkfriidfalsncinsgirrmgvitqyqshtlvqhiq
rgwsffneemnefvdllpaqqrmkgenwyrgtadavtqnldiirrykaeyvvilagdhiykqdysrmlidhvekgarctv
acmpvpieeasafgvmavdendkiiefvekpanppsmpndpskslasmgiyvfdadylyelleeddrdensshdfgkd
lipkiteaglayahpfplscvqsdpdaepywrdvgtleaywkanldlasvvdkldmydmwpirtyneslppakfvqdrs
gshgmtlnslvsggcvisgsvvvqsvlfsrvrvnsfcnidsavllpevwvgrscrlrrcvidracvipegmvigenaeedarr
fyrseegivlvtremlrklghkqer** (SEQ ID NO:3)

Figure 3

*glgC3* **Mutant *E. coli* ADP-glucose pyrophosphorylase (P295D, E296K) nucleotide sequence, as disclosed in WO 98/44780:**

atggttagtttagagaagaacgatcacttaatgttggcgcgccagctgccattgaaatctgttgccctgatactggcgggaggacg
tggtacccgcctgaaggatttaaccaataagcgagcaaaaccggccgtacacttcggcggtaagttccgcattatcgactttgcg
ctgtctaactgcatcaactccgggatccgtcgtatgggcgtgatcacccagtaccagtcccacactctggtgcagcacattcagc
gcggctggtcattcttcaatgaagaaatgaacgagtttgtcgatctgctgccagcacagcagagaatgaaaggggaaaactggt
atcgcggcaccgcagatgcggtcacccaaaacctcgacattatccgccgttataaagcggaatacgtggtgatcctggcgggc
gaccatatctacaagcaagactactcgcgtatgcttatcgatcacgtcgaaaaaggcgcacgttgcaccgttgcttgtatgccagt
accgattgaagaagcctccgcatttggcgttatggcggttgatgagaacgataaaattatcgaattcgttgaaaaacctgctaacc
cgccgtcaatgccgaacgatccgagcaaatctctggcgagtatgggtatctacgtctttgacgccgactatctgtatgaactgctg
gaagaagacgatcgcgatgagaactccagccacgactttggcaaagatttgattcccaagatcaccgaagccggtctggcctat
gcgcacccgttcccgctctcttgcgtacaatccgacccggatgccgagccgtactggcgcgatgtgggtacgctggaagcttac
tggaaagcgaacctcgatctggcctctgtggtggacaaactggatatgtacgatcgcaattggccaattcgcacctacaatgaat
cattaccgccagcgaaattcgtgcaggatcgctccggtagccacgggatgacccttaactcactggtttccggcggttgtgtgat
ctccggttcggtggtggtgcagtccgttctgttctcgcgcgttcgcgtgaattcattctgcaacattgattccgccgtattgttaccgg
aagtatgggtaggtcgctcgtgccgtctgcgccgctgcgtcatcgatcgtgcttgtgttattccggaaggcatggtgattggtgaa
aacgcagaggaagatgcacgtcgtttctatcgttcagaagaaggcatcgtgctggtaacgcgcgaaatgctacggaagttaggg
cataaacaggagcgataa (SEQ ID NO:4)

**Codon-optimized, glgC3 mutant *E. coli* ADP-glucose pyrophosphorylase (P295D, E296K) nucleotide sequence:**

atggtgagcctggagaagaacgaccacctgatgctggccaggcagctgccgctgaagagcgtggccctgatcctggccggc
ggcaggggtaccaggctgaaggacctgaccaacaagagggccaagccggccgtgcacttcggcggcaagttcaggatcatc
gacttcgccctgagcaactgcatcaacagcggcatcaggaggatgggcgtgatcacccagtaccagagccacaccctggtgc
agcacatccagagggggctggagcttcttcaacgaggagatgaacgagttcgtggacctgctgccggcccagcagaggatgaa
gggcgagaactggtacaggggcaccgccgacgccgtgacccagaacctggacatcatcaggaggtacaaggccgagtacg
tggtgatcctggccggcgaccacatctacaagcaggactacagcaggatgctgatcgaccacgtggagaagggcgccaggtg
caccgtggcctgcatgccggtgccgatcgaggaggccagcgccttcggcgtgatggccgtggacgagaacgacaagatcat
cgagttcgtggagaagccggccaacccgccgagcatgccgaacgacccgagcaagagcctggccagcatgggcatctacgt
gttcgacgccgactacctgtacgagctgctggaggaggacgacagggacgagaacagcagccacgacttcggcaaggacct
gatcccgaagatcaccgaggccggcctggcctacgccaccccgttcccgctgagctgcgtgcagagcgacccggacgccga
gccgtactggagggacgtgggcacCctggaggcctactggaaggccaacctggacctggccagcgtggtggacaagctgga
catgtacgacaggaactggccgatcaggacctacaacgagagcctgccgccggccaagttcgtgcaggacaggagcggcag
ccacggcatgaccctgaacagcctggtgagcggcggctgcgtgatcagcggcagcgtggtggtgcagagcgtgctgttcagc
agggtgagggtgaacagcttctgcaacatcgacagcgccgtgctgctgccggaggtgtgggtgggcaggagctgcaggctg
aggaggtgcgtgatcgacagggcctgcgtgatcccggagggcatggtgatcggcgagaacgccgaggaggacgccagga
ggttctacaggagcgaggagggcatcgtgctggtgaccagggagatgctgaggaagctgggccacaagcaggagaggtgat
ag (SEQ ID NO:5)

Figure 5

Kinetic properties of GlgC3

| Ligand | Enzyme | +FBP ($S_{0.5}$, $A_{0.5}$, or $I_{0.5}$) (μM) | -FBP ($S_{0.5}$, $A_{0.5}$, or $I_{0.5}$) (μM) |
|---|---|---|---|
| FBP | WT[a] | - | 50.4 ± 4 |
|  | G336D[a] | - | 9 ± 2 |
|  | P295D | - | 1.2 ± 2 |
|  | GlgC3 | - | 1.5 ± 2 |
| AMP | WT[a] | 94.7 ± 7 | - |
|  | G336D[a] | 860 | 17 |
|  | P295D | 1481 ± 43 | 478 ± 122 |
|  | GlgC3 | 5443 ± 98 | 5373 ± 55 |
| ATP | WT[a] | 300 ± 20 | 2200 ± 700 |
|  | G336D[a] | 130 ± 20 | 610 ± 30 |
|  | P295D | 250 ± 56 | 585 ± 183 |
|  | GlgC3 | 135 ± 17 | 109 ± 37 |

[a] Values as determined in Meyer et al., 1998, Arch. Biochem. Biophys. 352: 247-254

Figure 6

Kinetic Properties of GlgC3

| AMP(mM) | GlgC3 – FBP | GlgC3 + FBP | P295D – FBP | P295D + FBP |
|---|---|---|---|---|
| 10 | 18.98 | 18.54 | 7.81 | 6.4575 |
| 7.5 | 26.82 | 27.455 | 10.96 | 11.59 |
| 5 | 37.35 | 38.58 | 16.39 | 16.49 |
| 2 | 57.293 | 68.64 | 23.63 | 36.185 |
| 1.5 | 57.81 | 71.98 | 28.68 | 44.79 |
| 1 | 64.36 | 76.53 | 32.77 | 56.345 |
| 0.75 | 66.49 | 79.05 | 33.305 | 61.895 |
| 0.5 | 66.54 | 77.025 | 37.618 | 71.555 |
| 0.25 | 66.82 | 77.185 | 39.45 | 80.8775 |
| 0.1 | 68.83 | 75.615 | 43.075 | 83.575 |
| 0.05 | 70.97 | 74.11 | 47.025 | 82.083 |
| 0.025 | 66.05 | 72.65 | 55.385 | 83.78 |
| 0 | 55.475 | 74.735 | 76.088 | 84.96 |

Figure 7

Transgene Copy Number in *glgC3* Events

| Events | Copy number | Number of Intact Gene Copies |
|---|---|---|
| EC2A1143 | 1 | 1 |
| EC2A1148 | 1 | 1 |
| EC2A1152 | 1 | 1 |
| EC2A1224 | 1 | 1 |
| EC2A1237 | 2 | 2 |
| EC2A1238 | 1 | 1 |

Figure 8

Activity of AGPase in inbred and hybrid corn seed

| Inbred Events | | Hybrid Events | |
|---|---|---|---|
| Pedigree | specific activity (μmol/min/mg) | Pedigree | specific activity (μmol/min/mg) |
| Inbred A | 0.02 ± 0.01 | Inbred A* TR7322 | 0.01 ± 0.01 |
| EC2A1224 | 0.44 ± 0.10 | TR7322 * EC2A1224 | 0.27 ± 0.10 |
| EC2A1238 | 0.65 ± 0.17 | TR7322 * EC2A1238 | 0.45 ± 0.14 |

Figure 9

Grain Nutrient Composition of *glgC3* Inbreds Grown in Summer 2002

| Inbred | 2002 Nutrient Content (% of dry weight) | | | | | | |
|---|---|---|---|---|---|---|---|
| | EC2A1143 | EC2A1152 | EC2A1224 | EC2A1237 | EC2A1238 | EC1A1269 | Inbred A |
| Aspartic Acid | 0.75 ± 0.00 | 0.73 ± 0.01 | 0.79 ± 0.00 | 0.79 ± 0.01 | 0.78 ± 0.01 | 0.70 ± 0.00 | 0.67 ± 0.01 |
| Isoleucine | 0.37 ± 0.01 | 0.36 ± 0.01 | 0.4 ± 0.01 | 0.39 ± 0.01 | 0.36 ± 0.01 | 0.38 ± 0.01 | 0.34 ± 0.01 |
| Histidine | 0.30 ± 0.01 | 0.30 ± 0.01 | 0.31 ± 0.01 | 0.30 ± 0.01 | 0.29 ± 0.00 | 0.29 ± 0.00 | 0.27 ± 0.01 |
| Threonine | 0.39 ± 0.00 | 0.39 ± 0.01 | 0.41 ± 0.01 | 0.4 ± 0.00 | 0.4 ± 0.00 | 0.38 ± 0.00 | 0.36 ± 0.00 |
| Glycine | 0.45 ± 0.01 | 0.44 ± 0.00 | 0.46 ± 0.00 | 0.48 ± 0.01 | 0.48 ± 0.00 | 0.41 ± 0.00 | 0.4 ± 0.01 |
| Valine | 0.52 ± 0.01 | 0.51 ± 0.01 | 0.56 ± 0.01 | 0.56 ± 0.01 | 0.55 ± 0.01 | 0.51 ± 0.01 | 0.49 ± 0.01 |
| Cysteine | 0.25 ± 0.01 | 0.25 ± 0.01 | 0.26 ± 0.00 | 0.26 ± 0.01 | 0.27 ± 0.01 | 0.25 ± 0.00 | 0.24 ± 0.01 |
| Methionine | 0.25 ± 0.01 | 0.24 ± 0.01 | 0.25 ± 0.01 | 0.25 ± 0.01 | 0.26 ± 0.01 | 0.22 ± 0.00 | 0.22 ± 0.01 |
| Lysine | 0.38 ± 0.00 | 0.38 ± 0.00 | 0.40 ± 0.01 | 0.41 ± 0.00 | 0.4 ± 0.00 | 0.32 ± 0.00 | 0.3 ± 0.00 |
| Arginine | 0.57 ± 0.01 | 0.57 ± 0.01 | 0.60 ± 0.00 | 0.61 ± 0.01 | 0.61 ± 0.01 | 0.51 ± 0.01 | 0.49 ± 0.01 |
| Tryptophan | 0.09 ± 0.01 | 0.08 ± 0.00 | 0.08 ± 0.01 | 0.09 ± 0.01 | 0.08 ± 0.01 | 0.08 ± 0.01 | 0.07 ± 0.00 |
| Crude Protein | 10.98 ± 0.04 | 10.92 ± 0.03 | 11.47 ± 0.06 | 11.17 ± 0.05 | 11.15 ± 0.12 | 10.84 ± 0.06 | 10.49 ± 0.07 |
| Crude Fat | 4.59 ± 0.01 | 4.69 ± 0.12 | 4.64 ± 0.03 | 4.77 ± 0.06 | 4.82 ± 0.03 | 3.36 ± 0.11 | 3.21 ± 0.12 |
| Starch | 60.51 ± 2.38 | 57.61 ± 1.20 | 60.91 ± 0.62 | 60.68 ± 1.12 | 61.50 ± 1.49 | 65.20 ± 0.70 | 64.69 ± 0.73 |

| | % Difference over Inbred A control | | | | | | |
|---|---|---|---|---|---|---|---|
| | EC2A1143 | EC2A1152 | EC2A1224 | EC2A1237 | EC2A1238 | EC1A1269 | |
| Aspartic Acid | 12 | 9.0 | 18 | 18 | 16 | 4.5 | |
| Isoleucine | 8.8 | 5.9 | 18 | 15 | 5.9 | 12 | |
| Histidine | 11 | 11 | 15 | 11 | 7.4 | 7.4 | |
| Threonine | 8.3 | 8.3 | 14 | 11 | 11 | 5.6 | |
| Glycine | 13 | 10 | 15 | 20 | 20 | 2.5 | |
| Valine | 6.1 | 4.1 | 14 | 14 | 12 | 4.1 | |
| Cysteine | 4.2 | 4.2 | 8.3 | 8.3 | 13 | 4.2 | |
| Methionine | 14 | 9.1 | 14 | 14 | 18 | 0 | |
| Lysine | 27 | 27 | 33 | 37 | 33 | 6.7 | |
| Arginine | 16 | 16 | 22 | 24 | 24 | 4.1 | |
| Tryptophan | 29 | 14 | 14 | 29 | 14 | 14 | |
| Crude Protein | 4.8 | 4.1 | 9.3 | 6.5 | 6.3 | 3.3 | |
| Crude Fat | 43 | 46 | 45 | 49 | 50 | 4.8 | |
| Starch | -6.5 | -11 | -6.2 | -6.2 | -4.9 | 0.79 | |

Figure 10

Grain Nutrient Composition of *glgC3* F2 grain
(F1 hybrid grown in summer 2003)

| | 2003 Nutrient Content (% of dry weight) | | |
|---|---|---|---|
| | TR7322xInbred A | TR7322xEC2A1152 | TR7322xEC2A1237 |
| Aspartic Acid | 0.68 ± 0.034 | 0.718 ± 0.036 | 0.774 ± 0.038 |
| Isoleucine | 0.372 ± 0.015 | 0.376 ± 0.024 | 0.39 ± 0.019 |
| Histidine | 0.288 ± 0.008 | 0.296 ± 0.011 | 0.31 ± 0.012 |
| Threonine | 0.36 ± 0.012 | 0.358 ± 0.015 | 0.386 ± 0.019 |
| Glycine | 0.386 ± 0.011 | 0.428 ± 0.015 | 0.454 ± 0.015 |
| Valine | 0.506 ± 0.015 | 0.546 ± 0.03 | 0.572 ± 0.023 |
| Cysteine | 0.228 ± 0.008 | 0.226 ± 0.011 | 0.232 ± 0.018 |
| Methionine | 0.206 ± 0.011 | 0.21 ± 0.014 | 0.228 ± 0.019 |
| Lysine | 0.298 ± 0.019 | 0.36 ± 0.007 | 0.402 ± 0.011 |
| Arginine | 0.484 ± 0.017 | 0.546 ± 0.015 | 0.59 ± 0.023 |
| Tryptophan | 0.072 ± 0.004 | 0.08 ± 0 | 0.084 ± 0.005 |
| Crude Protein | 10.714 ± 0.357 | 10.474 ± 0.515 | 11.124 ± 0.47 |
| Crude Fat | 4.158 ± 0.273 | 5.058 ± 0.275 | 4.954 ± 0.05 |
| Starch | 67.8 ± 0.011 | 64.5 ± 0.010 | 62.7 ± 0.016 |
| | % Difference over control hybrid | | |
| Aspartic Acid | | 5.59 | 13.8 |
| Threonine | | -0.556 | 7.22 |
| Glycine | | 10.9 | 17.6 |
| Valine | | 7.91 | 13.0 |
| Cysteine | | -0.877 | 1.75 |
| Methionine | | 1.94 | 10.7 |
| Lysine | | 20.8 | 34.9 |
| Arginine | | 12.8 | 21.9 |
| Tryptophan | | 11.1 | 16.7 |
| Crude Protein | | -2.24 | 3.83 |
| Crude Fat | | 21.6 | 19.1 |
| Starch | | -4.87 | -7.52 |

Figure 11

| 2004 Grain Composition (% dry weight) | | | | | | | | | | |
|---|---|---|---|---|---|---|---|---|---|---|
| Entry Name | Thr | Cys | Val | Met | Lys | Arg | Trp | Protein | Oil | Starch |
| Inbred A/TN7713 | 0.318 | 0.207 | 0.461 | 0.173 | 0.298 | 0.448 | 0.079 | 9.30 | 5.04 | 66 |
| EC2A1148/TN7713 | 0.340 | 0.213 | 0.499 | 0.188 | 0.347 | 0.507 | 0.086 | 9.89 | 5.92 | 63 |
| EC2A1152/TN7713 | 0.332 | 0.210 | 0.480 | 0.183 | 0.342 | 0.492 | 0.084 | 9.56 | 6.00 | 62 |
| Inbred A/TN7765 | 0.367 | 0.238 | 0.537 | 0.209 | 0.340 | 0.530 | 0.089 | 10.71 | 5.59 | 68 |
| EC2A1152/TN7765 | 0.380 | 0.244 | 0.549 | 0.218 | 0.392 | 0.587 | 0.096 | 10.64 | 6.63 | 65 |
| Inbred A/TR5753 | 0.317 | 0.216 | 0.456 | 0.191 | 0.289 | 0.443 | 0.075 | 9.22 | 3.84 | 65 |
| EC2A1143/TR5753 | 0.331 | 0.223 | 0.486 | 0.207 | 0.335 | 0.495 | 0.081 | 9.68 | 4.59 | 65 |
| EC2A1148/TR5753 | 0.347 | 0.226 | 0.509 | 0.208 | 0.347 | 0.519 | 0.084 | 10.18 | 4.67 | 64 |
| EC2A1152/TR5753 | 0.334 | 0.222 | 0.488 | 0.206 | 0.336 | 0.498 | 0.081 | 9.72 | 4.57 | 65 |
| 2004 Grain Composition (% change over respective isoline) | | | | | | | | | | |
| Entry Name | Thr | Cys | Val | Met | Lys | Arg | Trp | Protein | Oil | Starch |
| EC2A1148/TN7713 | 6.9 | 2.9 | 8.2 | 8.7 | 16.3 | 13.2 | 8.9 | 6.3 | 17.5 | -4.9 |
| EC2A1152/TN7713 | 4.4 | 1.4 | 4.1 | 5.8 | 14.7 | 9.8 | 6.3 | 2.8 | 19.0 | -6.0 |
| EC2A1152/TN7765 | 4.3 | 2.5 | 2.8 | 5.2 | 15.4 | 11.2 | 9.2 | 0.4 | 18.8 | -4.4 |
| EC2A1143/TR5753 | 4.4 | 3.2 | 6.6 | 8.4 | 15.9 | 11.7 | 8.0 | 5.0 | 19.5 | 0.0 |
| EC2A1148/TR5753 | 9.6 | 4.6 | 11.6 | 8.9 | 20.2 | 17.2 | 12.0 | 10.4 | 21.6 | -1.5 |
| EC2A1152/TR5753 | 5.4 | 2.8 | 7.0 | 7.9 | 16.3 | 12.4 | 8.0 | 5.4 | 19.0 | 0.0 |

Figure 12

**Increased Embryo Weight in *glgC3* Transgenic Inbred Seed**

| 2003 selfed inbred | Percentage of Whole Seed Dry Weight | | | % Increase in embryo weight over Inbred A |
|---|---|---|---|---|
| Inbred | % Pericarp | % Endosperm | % Embryo | |
| EC2A1143 | 5.59 | 76.06 | 18.35 | 36 |
| EC2A1148 | 5.32 | 75.15 | 19.53 | 48 |
| EC2A1152 | 5.40 | 75.14 | 19.46 | 44 |
| Inbred A | 6.49 | 80.05 | 13.46 | 0 |

**Increased Embryo Weight in *glgC3* Transgenic Hybrid (F2 Grain)**

| | Percentage of Whole seed Dry Weight | | | % Increase in embryo weight over Control Hybrid |
|---|---|---|---|---|
| Hybrid | % Pericarp | % Endosperm | % Embryo | |
| TR7322xEC2A1143 | 6.69 | 79.05 | 14.26 | 40 |
| TR7322xEC2A1152 | 5.37 | 78.69 | 15.94 | 57 |
| TR7322xInbred A | 3.97 | 85.87 | 10.16 | 0 |

Figure 13

TRANSGENIC CORN HAVING ENHANCED NUTRITIONAL QUALITIES

CROSS REFERENCE TO RELATED APPLICATIONS

This application claims the benefit of U.S. provisional application No. 60/564,030, filed Apr. 21, 2004.

BACKGROUND OF THE INVENTION

Cereal grain is one of the most important renewable energy sources for humans and animals. Since over 90% of corn grain is used for animal feed, corn is one of the most important crops for animal nutrition. Grain of non-specialty yellow dent corn consists of 60-70% starch, 8-10% protein, and 3-4% oil. However, despite these valuable feed components, non-specialty yellow dent corn does not contain sufficient calories and essential amino acids to support optimal growth and development in most animals. Therefore, to compensate for these shortcomings, it is necessary to supplement yellow dent corn-based feed. Most commonly, yellow dent corn is supplemented with soybean meal and amino acids to improve the amino acid composition and caloric density of the feed. Unfortunately, animals lack the enzymes necessary to digest the non-starch based polysaccharides present in soybean meal, and corn/soybean feed mixtures result in high manure volume. In addition, soybean meal is expensive. Furthermore, to improve caloric content, corn-based animal feed is also supplemented with fats, such as animal offal and feed-grade animal and vegetable fats, which may include by-products of the restaurant, soap, and refinery industries. Use of animal offal to supplement cattle feed has been discontinued because of its association with bovine spongiform encephalopathy and Creutzfeldt-Jakob disease. Improvements to the nutritional qualities of corn grain will increase feed efficiency and reduce environmental impact and other costs associated with meat production.

The developing cereal grain seed is a remarkable factory, composed of pericarp, embryo, and endosperm. Most oil is synthesized and stored in the embryo, while the endosperm tissue contains the starch-based energy store. Protein is stored both in the embryo and endosperm. In all cereal crop plants, sucrose is delivered to the seed from the leaves and converted into hexose sugars, such as glucose, which in combination with amino acids is used for metabolism and synthesis of storage compounds such as starch, protein, and oil.

Since starch comprises 70% of cereal grain dry weight, starch biosynthesis plays an important role in determining seed yield and quality. The committed steps of starch biosynthesis involve at least three enzymatic reactions. First, adenosine diphosphate glucose (ADPG) is synthesized from glucose 1-phosphate and adenosine triphosphate (ATP), a reaction which is catalyzed by ADP-glucose pyrophosphorylase (AGPase). Then, starch synthase elongates α-1,4 glucan chains by transferring glucose from ADPG to an acceptor chain. Finally, branching enzyme hydrolyzes an elongated α-1,4 glucan chain and simultaneously transfers it to an acceptor chain to form an α-1,6 linkage.

In cereal grain seed endosperm tissue cells, the conversion of glucose to ADPG by AGPase occurs primarily in the cytosol, and ADPG is imported into the amyloplast by a specific ADPG transporter protein. There is minor AGPase activity in the endosperm amyloplast compartment (hereinafter referred to as the plastid or plastid compartment) of monocots. In corn endosperm, for example, the plastidial AGPase activity represents less than ten percent of the overall AGPase activity of the seed. In contrast, in dicot crops AGPase is localized primarily (and possibly exclusively) in the plastid, synthesizing ADPG primarily in the plastid compartment of the cell. Since AGPase is encoded by a nuclear gene, localization of AGPase in the plastid requires that the protein be first expressed in the cytosol and then translocated into the plastid by a plastid transit peptide. If the plastid transit peptide is lacking, the plant's AGPase activity will remain in the cytosol.

AGPase is considered one of the limiting steps in starch biosynthesis in plants and glycogen synthesis in bacteria. Much effort has been focused on improving seed quality by genetic engineering of AGPase to change starch content of cereal grain seeds.

U.S. Pat. No. 5,792,920 discloses isolation of genes encoding AGPases from wheat endosperm and leaf. U.S. Pat. No. 5,792,920 further discloses incorporation of the disclosed genes into a cereal plant genome in the sense or antisense direction, to improve or reduce the plant's ability to synthesize starch.

U.S. Pat. Nos. 5,498,831 and 5,773,693 disclose cDNAs encoding the large subunit (SH2) and small subunit (BT2) of pea AGPase. U.S. Pat. Nos. 5,498,831 and 5,773,693 also disclose that overexpression of these genes requires a plastid transit sequence for proper sub-localization of the heterotetrameric enzyme.

U.S. Pat. No. 6,232,529 discloses a method for enhancing accumulation of oil beyond normal levels in the embryo of a corn seed, by reducing starch production by diminishing or abolishing the activity of AGPase in the embryo, but not in other tissue.

U.S. Pat. No. 6,486,383 discloses transgenic potato plants containing either the wheat brittle 2 gene (the small subunit of wheat AGPase) or the wheat shrunken-2 gene (the large subunit of wheat AGPase). The transgenic potato plants of U.S. Pat. No. 6,486,383 demonstrated increased AGPase activity.

WO 93/09237 discloses a method of improving the starch and sugar content to sweet corn by manipulating the timing of expression of the sh-2 (large) and bt-2 (small) subunits of the heterotetrameric maize AGPase.

WO 94/24292 discloses DNA sequences of the large and small subunits of the barley endosperm AGPase, including targeting expression of either or both subunits to plant endosperm tissue using DNA sequences encoding transit peptides.

WO 98/10082 discloses a mutant of the maize Sh2 (AGPase large subunit) gene designated Sh2-m1Rev6, which results in increased seed weight, but which demonstrates no higher percentage of starch as compared to other Sh2 alleles.

WO 98/22601 and WO 99/58698 disclose mutants of the maize endosperm large subunit gene, which are purported to improve yield when present in plants grown under heat stress.

WO 99/07841 discloses up-regulated allosteric mutants of plant AGPases, which result in increased starch production, increased yield, increased plant size, increased growth rate, and increased numbers of seeds when transformed into *Arabidopsis*.

U.S. Pat. Nos. 5,349,123; 5,969,214; and 6,538,181 disclose DNA sequences encoding bacterial glycogen biosynthetic enzymes, including a glgC mutant derived from *E. coli* 618 designated pGlgC-37. U.S. Pat. Nos. 5,349,123; 5,969,214; and 6,538,181 state that the AGPase from *E. coli* 618 differs from that of *E. coli* K12 at five amino acids, and that the translated amino acid sequences of pGlgC-37 differs from the AGPase of *E. coli* 618 only at position 361, by a substitution of aspartate for asparagine. U.S. Pat. Nos. 5,349,123; 5,969,214; and 6,538,181 also disclose joining the bacterial glycogen synthetic enzyme genes with a sequence encoding a transit peptide that provides for translocation of the enzyme to a plastid of a plant. These patents predicted that expressing bacterial glycogen biosynthetic enzymes in plant plastids would result in modulation of the starch content of the plant.

The AGPase from *E. coli* 618 has been extensively studied. Lee, et al. (1987) *Nucleic Acids Res.* 15, 10603 also discloses that the AGPase from strain 618 differs from that of *E. coli* K12 strain 3000 (commonly designated as the wild type enzyme) at five amino acid residues, valine to alanine at position 161, valine to alanine at position 166, threonine to isoleucine at position 189, lysine to glutamate at position 296, and glycine to aspartate at position 336. However, Kumar, et al. (1989) *J. Biol. Chem.* 264, 10464-10471 discloses that the substitutions at positions 161, 166, and 189 previously reported for the 618 AGPase were sequencing errors, and that the 618 enzyme did not differ from the wild type AGPase at these three positions. Furthermore, Meyer, et al. (1993) reported that the sequence of the wild type enzyme at position 296 is glutamate and not lysine as previously reported, and thus that the 618 AGPase differs from the wild type enzyme only by the glycine to aspartate substitution at position 336.

U.S. Pat. No. 6,538,178, related U.S. Pat. Nos. 6,538,179; 5,498,830 and 5,608,149, WO 91/19806, and EP 634491 disclose that transformation into plants of wild type and mutant *E. coli* AGPase genes, including the mutant gene from strain 618 (designated therein as glgC16), in fusion with a plastid targeting transit peptide, results in increased starch content. U.S. Pat. No. 6,538,178 specifically exemplifes increases in starch content of transformed tobacco callus, potatoes, and tomato. U.S. Pat. Nos. 5,498,830 and 6,538,179, continuations-in-part of the parent application of U.S. Pat. No. 6,538,178, disclose additional transformations of a plastid transit peptide-glgC16 gene fusion into potato, tomato, canola, and maize. U.S. Pat. Nos. 5,498,830 and 6,538,179 disclose that canola seeds transformed with a plastid transit peptide-glgC16 gene fusion demonstrated increased starch content and decreased oil content, while protein content and moisture were not significantly changed. U.S. Pat. Nos. 5,498,830 and 6,538,179 further disclose that maize Black Mexican Sweet callus transformed with a plastid transit peptide-glgC16 gene fusion demonstrated two to threefold increases in starch levels, as compared with control lines.

Sakulsingharoj, et al (2004) *Plant Science* 167, 1323-1333 discloses rice transformed with an *E. coli* AGPase triple mutant (described therein as R67K, P295D, G366D), which displays up to 90% of the catalytic activity of the fully activated wild-type enzyme in the absence of any activators. The triple mutant AGPase gene was transformed both with and without a transit peptide sequence, under control of the rice glutelin Gt1 promoter. Rice transformants thus generated expressed the bacterial enzyme either in the amyloplast or in the cytoplasm of developing seeds. The authors noted a positive correlation between increases in cytoplasmic AGPase activity, $^{14}$C-sucrose incorporation into starch, and seed weight. However, rice plants exhibiting elevated AGPase activity in amyloplast exhibited variable responses.

U.S. Pat. No. 6,483,011 discloses methods for generating AGPase mutants, which increase starch formation, or which increase the accumulation or depletion of certain starches. U.S. Pat. No. 6,483,011 discloses a mutant *E. coli* strain, which lacks AGPase activity and carries an unknown mutation in the *E. coli* glgC gene designated glgC3. The glgC3 disclosed in U.S. Pat. No. 6,483,011 is a loss of function mutant.

WO 98/44780 discloses the DNA and protein sequences of a mutant AGPase from *E. coli* designated glgC3, which contains two mutations, a proline to aspartic acid substitution at amino acid 295 and a glutamic acid to lysine substitution at amino acid 296. Rice transformants containing the glgC3 gene are also disclosed in WO 98/44780.

Bacterial AGPase is a homotetramer encoded by the glgC gene, while plant AGPase is a heterotetramer. Based on specificity for activator and inhibitor, AGPases have been grouped into classes 1 through VII, as summarized in Ballicora et al. (2003) *Microbio. Mol. Biol. Rev.* 67, 213-225, Table 1. With some exceptions, prokaryotic AGPases are activated by fructose-1,6-bis-phosphate (FBP), and inhibited by adenosine monophosphate (AMP), and higher plant AGPases are activated by 3-phosphoglycerate (3-PGA) and inhibited by inorganic phosphate.

U.S. Pat. Nos. 4,885,357; 4,886,878; 5,003,045; 5,576,203; 5,487,991; 5,589,615; 5,623,067; 5,258,300; 5,082,993; 5,589,616; 5,215,912; 5,367,110; 5,559,223; 5,451,516; 5,633,436; 5,530,192; 5,545,545; and 5,633,436 disclose various methods for genetic engineering of plants to increase the content of one or more amino acids. Since the amino acid content of seed is primarily (90-99%) determined by the bound amino acid (protein composition) and to a much less extent (1-10%) by the free amino acid pool, there are serious challenges to approaches which result in increases of free amino acids to improve nutritional value. One challenge is that increased free amino acid concentration is not always associated with an increase in total amino acid, since the free amino acid content is such a small percentage of the total amino acid and the flux and incorporation of free amino acid into protein may become limiting. Secondly, due to accumulation of free amino acids or reduced amino acid catabolism, amino acid changes in these studies are often associated with adverse agronomic performance, such as stunted growth, therefore affecting marketability. Third, the targeted approach often leads to changes in one or two amino acids, which may limit the market value of the grain so produced.

A need continues to exist for corn grain with increased levels of certain amino acids and oil, and which has desirable agronomic characteristics.

SUMMARY OF THE INVENTION

The present inventors have surprisingly found that expressing a gene encoding the GlgC3 protein of WO 98/44780 in endosperm plastids of transgenic corn seed results in significantly higher levels of oil and a number of amino acids when compared to isogenic corn seed which does not express the GlgC3 protein in endosperm plastids. However, the starch content of transgenic corn seed expressing the GlgC3 protein of WO 98/44780 in endosperm plastids is decreased or not changed when compared to the starch content of isogenic corn seed which does not express the GlgC3 protein in endosperm plastids. Moreover, the embryo weight in the transgenic corn seed of the invention is at least about 5% larger than the embryo mass of isogenic corn seed which does not express the GlgC3 protein in endosperm plastids.

In one embodiment, the invention provides a transgenic corn seed expressing an enzymatically active GlgC3 protein in an endosperm plastid of said seed, wherein, when compared to an isogenic corn seed which does not express the GlgC3 protein in an endosperm plastid, said transgenic corn seed is characterized by: an increase of at least about 5% in oil content over the oil content of said isogenic corn seed; increases of at least about 5% in any three amino acids selected from the group consisting of aspartic acid, threonine, glycine, cysteine, valine, methionine, isoleucine, histidine, lysine, arginine, and tryptophan; and a starch content which is decreased or not changed when compared to the starch content of said isogenic corn seed.

In another embodiment, the invention provides a transgenic corn seed expressing an enzymatically active exogenous AGPase in an endosperm plastid of said seed, wherein the enzymatic activity of said AGPase is not significantly inhibited by an inhibitor of said AGPase in the absence of an activator of said AGPase.

BRIEF DESCRIPTION OF THE DRAWINGS

FIG. 1 shows the sequence of the wild type *E. coli* GlgC protein (GenBank accession number: AAC76455, SEQ ID NO:1).

FIG. 2 shows the sequence of the wild type *E. coli* glgC gene (GenBank accession number: AE000419 region: complement (4442.5737), SEQ ID NO:2).

FIG. 3 shows the sequence of the *E. coli* GlgC3 protein, as set forth in WO 98/44780 (SEQ ID NO:3).

FIG. 4 shows the sequence of the *E. coli* glgC3 gene, as set forth in WO 98/44780 (SEQ ID NO:4).

FIG. 5 shows the sequence of the plant codon-optimized *E. coli* glgC3 gene (SEQ ID NO:5).

FIG. 6 is a table depicting the kinetic properties of the GlgC3 AGPase.

FIG. 7 is a table depicting the kinetic properties of the GlgC3 AGPase.

FIG. 8 is a table depicting transgene copy number of several transgenic maize events containing the glgC3 gene.

FIG. 9 is a table comparing AGPase activity measured in transgenic maize events comprising the glgC3 gene and in an isogenic control.

FIG. 10 is a table showing compositional analysis of a number of transgenic maize events comprising the glgC3 gene and of an isogenic control inbred.

FIG. 11 is a table showing compositional analysis of F2 grains from F1 hybrid transgenic maize events comprising the glgC3 gene and from an isogenic control hybrid.

FIG. 12 is a table showing compositional analysis of F2 grains from F1 hybrid transgenic maize events comprising the glgC3 gene and from isogenic control hybrids.

FIG. 13 shows two tables: one table compares weight measurements of pericarp, endosperm, and embryo in transgenic maize events comprising the glgC3 gene with an isogenic control inbred, and the other table compares weight measurements of pericarp, endosperm, and embryo in F2 grain from F1 hybrid transgenic maize events comprising the glgC3 gene and from an isogenic control hybrid.

DETAILED DESCRIPTION OF THE INVENTION

"Transgenic corn seed" as used herein means a corn seed having a non-native gene (also referred to as the transgene of interest) stably incorporated into the seed genome. "Non-native" means a gene that is not present or native to the original parent of the corn seed. "Corn seed" may be seed from an inbred corn line or any corn seed including an F1 hybrid (that is, a cross of a male inbred line with a female inbred line), or F2 corn seed (that is, grain grown from F1 hybrids) and any corn population. F2 grain is the commercial grain used for animal feed.

"Isogenic corn seed" means the untransformed parental inbred or other corn seed which does not express the transgene of interest and from which the transgenic corn seed of the invention is derived.

"glgC3," when used in reference to any aspect of the present invention, means a nucleic acid encoding a mutant AGPase protein from *E. coli*, designated GlgC3, as disclosed in WO 98/44780, containing two mutations, a proline to aspartic acid substitution at amino acid 295, and a glutamic acid to lysine substitution at amino acid 296. In accordance with the invention, the glgC3 gene used to express the mutant AGPase is codon-optimized for expression in plants, for example, as set forth in FIG. 5 and SEQ ID NO:5.

"Enzymatically active," when used in reference to an AGPase, such as the GlgC3 protein, means that transgenic maize inbreds and hybrids expressing the exogenous AGPase demonstrate an increase in AGPase activity when compared, under the same assay conditions, to an isogenic control maize inbred or hybrid which does not contain the gene encoding the exogenous AGPase.

"Exogenous" means that, as the result of expression of a non-native gene, an AGPase is expressed in endosperm plastids of a transgenic corn seed, which AGPase is not expressed in endosperm plastids of a corn seed isogenic to the transgenic corn seed.

"Inhibitor", when used in reference to an AGPase in accordance with the invention, means an allosteric regulator which decreases the enzymatic activity of the AGPase. For example, as indicated in Table 1 of Ballicora, et al., supra, AMP is an inhibitor of AGPases of Classes I, II, III, IV, and V; adenosine diphosphate (ADP) is an inhibitor of AGPases of Classes II, IV, and IX; inorganic phosphate ($P_i$) is an inhibitor of AGPases of Classes V, VIII, and IX; and FBP is an inhibitor of Class IX AGPases.

"Activator" when used in reference to an AGPase in accordance with the invention, means an allosteric regulator which increases the enzymatic activity of the AGPase. For example, as indicated in Table 1 of Ballicora, et al., supra, FBP is an activator of AGPases of Classes I, II, and V; fructose 6-phosphate is an activator of AGPases of Classes II, IV, and V; pyruvate is an activator of AGPases of Classes IV, V, and VI; and 3-PGA is an activator of AGPases of Class VIII. In accordance with the invention, although they are not direct allosteric regulators of Class IX AGPases, 3-PGA and fructose 6-phosphate are activators of Class IX AGPases, by virtue of their ability to reverse an inhibitor's effect.

In accordance with the invention, an enzymatically active exogenous AGPase protein encompasses any level of increased AGPase activity over that of an isogenic control. Preferably, the AGPase activity demonstrated by an enzymatically active AGPase protein in the transgenic corn seed of the invention will be increased by a range of about twofold to about 45-fold. More preferably, the AGPase activity demonstrated by an enzymatically active exogenous AGPase protein in the transgenic corn seed of the invention will be increased by a range of about tenfold to about 45-fold. Most preferably, the AGPase activity demonstrated by an enzymatically active exogenous AGPase protein in the transgenic corn seed of the invention will be increased by a range of about 20-fold to about 45-fold.

"Amino acid content," as used herein, means the amount of total amino acids, including free amino acids and bound amino acids in the form of protein.

All percentages of amino acids, protein, oil, and starch recited herein are percent dry weight.

The transgenic corn seed of the invention is characterized by increases in at least three amino acids. Any three amino acids may be increased in accordance with the invention. Preferably, the amino acids which are increased in the transgenic corn seed of the invention are selected from the group consisting of aspartic acid, threonine, glycine, cysteine, valine, methionine, isoleucine, histidine, lysine, arginine, and tryptophan. More preferably, the transgenic corn seed of the invention demonstrates increases of at least about 5% in at least three amino acids selected from the group consisting of aspartic acid, threonine, glycine, cysteine, valine, methionine, isoleucine, histidine, lysine, arginine, and tryptophan. Most preferably, the transgenic corn seed of the invention demonstrates increases of at least about 5% in amino acids selected from the group consisting of threonine, cysteine, valine, methionine, lysine, arginine and tryptophan. For example, in one preferred embodiment, tryptophan, arginine, and lysine are increased by at least about 5% in the transgenic corn seed of the invention. In another preferred embodiment, valine, lysine, and tryptophan are increased by at least about 5% in the transgenic corn of the invention. In yet another preferred embodiment, valine, methionine, and lysine are increased by at least about 5% in the transgenic corn of the invention, and so forth.

In addition to the amino acid increases described above, the transgenic corn seed of the invention is characterized by an increase in oil content of at least about 5% over the oil content of isogenic corn seed which does not express the GlgC3 protein in endosperm plastids. More preferably, the oil content of the transgenic corn seed of the invention is increased by at least about 10% over the oil content of isogenic corn seed which does not express the GlgC3 protein in endosperm plastids. Most preferably, the oil content of the transgenic corn seed of the invention is increased by at least about 15% over the oil content of isogenic corn seed which does not express the GlgC3 protein in endosperm plastids.

In addition to the increases in amino acids and oil content described above, the the transgenic corn seed of the invention is characterized by a starch content which is decreased or not changed when compared to an isogenic corn seed which does not express the glgC3 gene in endosperm plastids.

The inventors have also found that the size of the embryo or germ of the transgenic corn seed of the present invention is significantly increased over the size of embryos of germs of isogenic corn seed which does not express the glgC3 gene in endosperm plastids. By "significantly increased" is meant that a statistically significant increase is observed in the weight or mass of embryos of transgenic corn seed expressing the glgC3 gene in endosperm plastids as compared to embryos of isogenic corn seed which does not express the glgC3 gene in endosperm plastids. This increase in embryo size is observed in transgenic glgC3 inbred seed and in seed from hybrids made using transgenic glgC3 inbred seed, as shown in Example 7 below. Preferably, the size of the embryo of the transgenic corn seed of the invention is increased from about 5% to about 10% as compared to embryos of isogenic corn seed which does not express the glgC3 gene in endosperm plastids. More preferably, the size of the embryo of the transgenic corn seed of the invention is increased from about 10% to about 25% as compared to embryos of isogenic corn seed which does not express the glgC3 gene in endosperm plastids. Most preferably, the size of the embryo of the transgenic corn seed of the invention is increased from about 20% to about 35% as compared to embryos of isogenic corn seed which does not express the glgC3 gene in endosperm plastids.

FIGS. 6 and 7 depict the unique kinetic properties of the GlgC3 AGPase. Most notably, the GlgC3 AGPase, a Class I AGPase as indicated in Ballicora, et al., supra, is not significantly changed in the presence of the Class I inhibitor AMP, whether the Class I activator FBP is present or absent. In contrast, AMP does cause a threefold decrease in the activity of an *E. coli* AGPase containing the single mutation proline to aspartate at position 295 (designated P295D in FIGS. 6 and 7) when FBP is not present. In addition, the affinity of the GlgC3 AGPase for the substrate adenosine triphosphate (ATP) is substantially equivalent in the presence or absence of FBP. In contrast, the affinity of the P295D AGPase for ATP is substantially increased when FBP is present.

The invention is also embodied in a transgenic corn seed which expresses, in an endosperm plastid, an AGPase having kinetic properties similar to the GlgC3 AGPase. The transgenic corn seed of this embodiment expresses an enzymatically active exogenous AGPase in an endosperm plastid of said seed, wherein the enzymatic activity of said AGPase is not significantly inhibited by an inhibitor of said AGPase, in the absence of an activator of said AGPase. "Not significantly inhibited" means that when enzymatic activity of the purified exogenous AGPase is measured in vitro, its activity in the presence of the inhibitor at concentrations of up to 2 mM, and in the absence of activator, is more than 75% of its activity in the presence of said activator and up to 2 mM of said inhibitor.

The transgenic corn seed of the invention may be produced by transforming a gene encoding exogenous AGPase such as the glgC3 gene, in operative association with a plastid transit peptide, into a corn inbred or hybrid using any known method of transforming a monocot such as corn. For example, the AGPAse/transit peptide gene may be transformed into a corn inbred or hybrid using particle bombardment as set forth in U.S. Pat. Nos. 4,945,050; 5,036,006; 5,100,792; 5,302,523; 5,464,765; 5,120,657; 6,084,154; and the like. More preferably, the transgenic corn seed of the invention may be made using *Agrobacterium* transformation, as described in U.S. Pat. Nos. 5,591,616; 5,731,179; 5,981,840; 6,162,965; 6,420, 630, U.S. patent application publication number 2002/ 0104132, and the like. Since the glgC3 transgene is dominant, any corn inbred or hybrid may express the GlgC3 protein after being crossed to the transgenic corn. Alternatively, the transgenic corn seed of the invention may be produced using plastid transformation methods suitable for use in corn. Plastid transformation of tobacco is described, for example, in U.S. Pat. No. 6,541,682; Zoubenko, et al. (1994) *Nucleic Acids Res.* 22, 3819-3824; Ruf, et al. (2001) *Nature Biotechnol.* 19, 870-875; Kuroda et al. (2001) *Plant Physiol.* 125, 430-436; Kuroda et al. (2001) *Nucleic Acids Res.* 29, 970-975; Hajdukiewica et al. (2001) *Plant J.* 27, 161-170; and Corneille, et al. (2001) *Plant J.* 72, 171-178. Additional plastid transformation methods employing the phiC31 phage integrase are disclosed in Lutz, et al. (2004) *The Plant J.* 37, 906.

In accordance with the invention, the gene encoding an exogenous AGPase gene such as the glgC3 gene may be present on any expression cassette suitable for expression of a gene in a plastid in the endosperm of corn. Such an expression cassette comprises a promoter capable of directing expression in the endosperm of corn and a nucleotide sequence encoding a plastid transit peptide. Preferably, a promoter suitable for use in the expression cassette is a constitutive promoter, for example, a maize ubiquitin promoter or a maize branching enzyme-1 promoter. More preferably, a promoter suitable for use in the expression cassette is a seed specific promoter, such as a maize granule bound starch synthase promoter. Most preferably, a promoter used in the expression cassette is an endosperm-specific promoter, for example, a maize 10 kD zein promoter, a maize 19 kD zein promoter, or a maize 27 kD zein promoter. Promoters from species other than maize may also be used in accordance with the invention, so long as the promoter is capable of directing expression of nucleic acids in maize seed or endosperm tissue. Nucleotide sequences encoding plastid transit peptides are well known, as disclosed, for example, in U.S. Pat. Nos. 5,717,084; 5,728,925; 6,063,601; 6,130,366; and the like.

The expression cassette that includes the glgC3 gene may also contain suitable termination sequences and other regulatory sequences, which may optimize expression of the gene in plastids of the corn endosperm.

The potential for reducing costs associated with meat production using the transgenic corn seed of the invention is great. The improved amino acid profile of the transgenic corn of the invention allows it to be used in feed without soybean meal supplementation, thus eliminating the expense and environmental impact associated with feeds containing soybean meal. Moreover, the improved oil content of the transgenic corn seed of the invention will allow animal feed producers to minimize use of animal by-products as additives to animal feed, thus minimizing possible contamination of the human food chain with infectious agents such as the bovine spongiform encephalopathy agent. Farmers will be able to obtain a more optimal feed conversion ratio by replacing yellow dent corn-based feed with feed comprising the transgenic corn of the invention. The transgenic corn seed of the invention is therefore particularly useful as animal feed.

The invention is further illustrated by the following examples, which are not to be construed in any way as imposing limitations upon the scope thereof.

EXAMPLE 1

Generation and Characterization of gLGC3 Mutant

Two amino acid changes (P295D, E296K) were introduced into wild-type AGPase from *E. coli*(glgC: FIG. 1, which discloses the amino acid sequence of the GlgC protein (SEQ ID NO:1) and FIG. 2, which discloses the nucleotide sequence of the glgC gene (SEQ ID NO:2)) via in vitro site-directed mutagenesis as per manufacturer's instructions (QuikChange Site-Directed Mutagenesis Kit, Stratagene; Lajolla, Calif.). Site-directed mutagenesis was performed on a template glgC gene which encodes AGPase *E. coli* K12 using primer EXS42 (SEQ ID NO:6) and its reverse compliment, primer EXS43 (SEQ ID NO:7):

```
                                           (SEQ ID NO:6)
EXS42: 5' C TCT GTG GTG gac aAA CTG GAT ATG 3'

(SEQ ID NO:7)
EXS43: 5' CAT ATC CAG TTt gtc CAC CAC AGA G 3'
```

Nucleotides in the primers differing from wild-type sequence are in lower-case. Mutations introduced by site-directed mutagenesis were confirmed by DNA sequencing. This glgC double-mutant gene was named "glgC3 (FIG. 3, which discloses the amino acid sequence of the GlgC3 protein (SEQ ID NO:3) and FIG. 4, which discloses the nucleotide sequence of the glgC3 gene (SEQ ID NO:4)).

EXAMPLE 2

Kinetic Characterization of GlgC3 Enzyme

A. Protein Expression and Purification. GlgC3 was expressed in *E. coli* strain EX2 (glgA−, glgB−, glgC−, glgX−) and purified from eight liters of Luria-Bertanni broth (LB). Protein purification of GlgC3 AGPase was performed with modifications as previously described (Meyer et al., 1993, Arch. Biochem. Biophys. 302: 64-71; Meyer et al. 1998, Arch. Biochem. Biophys. 352: 247-254). The cell pellet was resuspended in 50 mM glycylglycine, pH 7.0, 1 mM EDTA, 5 mM dithiothreitol (DTT), 100 mg/L phenylmethanesulfonyl fluoride (PMSF), and 100 mg/L benzamidine. Resuspended cells were lysed using a Fisher 550 sonic dismembrator with six one-minute bursts with 30-second intervals on an output of eight. After sonication, sodium phosphate was added to a final concentration of 30 mM. The lysate was heat-treated at 55°Celsius for five minutes and cooled immediately on ice. More PMSF and benzamidine was added to the concentrations specified above. Ammonium sulfate was added to 41% saturation and the sample was stirred for one hour on ice. The sample was centrifuged at 14,000×g (12,000 rpm in a Sorvall SLA-1500 rotor) for 30 minutes. The pellet was resuspended in 50 mM Tris-acetate, pH 7.2, 5 mM DTT, 100 mg/L PMSF, and 100 mg/L benzamidine, and dialyzed overnight. After dialysis, the sample was centrifuged at 14,000 g (12,000 rpm in a Sorvall SLA-1500 rotor) for 25 minutes and the supernatant was filtered through a 0.22 μm filter. The sample was run on a Pharmacia FPLC with a MonoQ 10/10 column where Buffer A was 15 mM potassium phosphate, pH 7.5 and 5 mM DTT and Buffer B was 200 mM potassium phosphate, pH 7.0, 0.5 M KCl, and 5 mM DTT. A 0-50% gradient of buffer B in 160 ml at a flow rate of two ml/min was run and three ml fractions were collected. The fractions were assayed for enzyme activity and active fractions were pooled and dialyzed overnight against 50 mM Tris-acetate, pH 7.2, 1 mM EDTA, and 5 mM DTT. Sample was loaded onto a MonoQ 10/10 column where Buffer A is 50 mM Tris-acetate, pH 7.2, 1 mM EDTA, and 5 mM DTT. Buffer B is the same as Buffer A with the addition of 1 M KCl. A 0.0-0.2 M KCl gradient was run in 10 ml (flow rate 2 ml/min) and then a 0.2-0.6 M KCl gradient was run in 150 ml. Fractions were assayed for enzyme activity and separated on a Coomassie-stained SDS-polyacrylamide gel. Active fractions were pooled and glycerol was added to a final concentration of 20%. The purified protein was stored at −80° Celsius.

B. Enzyme Assays and Kinetic Analysis. Enzyme assays and kinetic analysis were run in the ADPG synthesis direction (Meyers et al., 1998, Arch. Biochem. Biophys. 352: 247-254). Standard assays contained 100 mM HEPES, pH 7.0, 0.5 mg/ml bovine serum albumin (BSA), 1.5 mM ATP, 5 mM MgCl2, and 1 mM $^{14}$C-glucose-1-phosphate (2000 dpm/nmol). Kinetics were performed in duplicate at two time points, 10 and 13 minutes, to ensure the reaction was in the linear range. The enzyme assay was either done with 1 mM fructose 1,6 bis-phosphate (FBP) or without FBP for kinetic analysis. Enzyme activity (μmol ADPG/min/mg protein) was measured with 1 mM FBP or without FBP. AMP concentration ranged from 0 to 10 mM. Assays on immature transgenic corn kernels were performed by grinding the kernels in 50 mM Tris-acetate, pH 8.0, 10 mM EDTA, and 5 mM DTT. The resulting homogenate was placed in an eppendorf tube and spun at 8,900 g (10,000 rpm in a Beckman Microfuge 18) for 10 minutes. The supernatant was used in the enzyme assay.

Compared with wild type GlgC, mutant P295D, and mutant G336D (GlgC16 as described in U.S. Pat. No. 6,538, 179), the GlgC3 mutant showed improved catalytic properties. (Wild type GlgC and mutant G336D were characterized by Meyer et al., 1998, Arch. Biochem. Biophys. 352: 247-254). In comparison to mutant G336D, GlgC3 is less dependent on activator FBP. In comparison to mutant G336D and mutant P295D, GlgC3 is much less sensitive to inhibitor AMP (FIG. 6). The activity of GlgC3 is not inhibited in the presence of 1 mM AMP with or without FBP (FIG. 7). Furthermore, it showed a higher affinity for substrate ATP in the absence of FBP (FIG. 6). The Km value for ATP is less than 0.15 mM in the presence or absence of FBP.

EXAMPLE 3

Codon-Optimization & Gene Synthesis

The nucleotide sequence of the glgC3 gene of Example 1 was altered to more closely reflect the bias in codon usage found in *Zea mays*. A first draft of the synthetic glgC3 sequence was written using the most prevalently-used codon for each amino acid according to *Zea mays* codon-usage tables from the Codon Usage Databas, an extended WWW version of CUTG (Codon Usage Tabulated from Genbank) that is developed and maintained by Yasukazu Nakamara at The First Laboratory for Plant Gene Research, Kazusa DNA Research Institute, Japan. This first draft was then modified to add or remove restriction sites by silent mutations. Unique Nco I and Not I restriction sites were included at the 5' and 3' ends of the gene, respectively, to allow for convenient subcloning. The plant codon-optimized glgC3 gene sequence is set forth in FIG. 5 and SEQ ID NO:5. Using this sequence, the plant codon-optimized glgC3 gene was synthesized using routine methods (Retrogen; San Diego, Calif.).

EXAMPLE 4

Construction of Transgenic Expression Cassette and Super-Binary Vector

The plant codon-optimized glgC3 gene of Example 3 was PCR amplified from a template plasmid designated "synthetic glgC3" using primer EXS233 (SEQ ID NO:8), which introduced a Nde I site at the 5' end of the plant codon-optimized glgC3, and the vector-specific primer EXS6 (SEQ ID NO:9):

```
                                         (SEQ ID NO:8)
EXS233:  GGAATTCCAT ATG GTG AGC CTG GAG AAG AAC GAC (SEQ ID NO:9)
EXS6:    TCACACAGGAAACAGCTATGAC
```

This PCR product was digested with Nde I and Not I and subcloned into a transgene expression cassette; the resulting plasmid was named pEXS222. The transgene expression cassette consisted of the 10 kDa zein promoter and 5' untranslated region from maize line A632 followed sequentially by the ferredoxin transit peptide from *Silene pratensis*, the plant codon-optimized glgC3 coding sequence, and the nopaline synthase (nos) terminator from *Agrobacterium tumefaciens* T-DNA. This transgene expression cassette was then subcloned into super-binary vector pSB11 for use in *Agrobacterium tumefaciens*-mediated transformation. glgC3 was transformed into an elite corn inbred designated herein as "Inbred A" via *Agrobacterium*-mediated transformation as described in patent Publication No US2002/0104132 A1.

EXAMPLE 5

Transgenic GLGC3 Expression Analysis

Mature transgenic kernels were analyzed by western blot to check for protein expression. Mature kernels were crushed in a single seed crusher and placed in a 96-well plate. One ml of 50 mM Tris-acetate, pH 8.0, 10 mM EDTA, and 5 mM DTT and 2 steel grinding balls were added to each well. The 96-well plates were then heat sealed and samples were homogenized in the Geno-Grinder at 1400 strokes/minute for 5 minutes. The 96-well plate was then spun at 4,700 g (5000 rpm in a Beckman Allegra 25R centrifuge S5700 rotor) for 10 minutes and the supernatant was saved. Approximately 10 µg of total protein was separated on a 10% SDS-PAGE gel. The gels were then blotted to nitrocellulose at 300 mA for 1 hour. A primary antibody raised against purified GlgC was used in a 1:1000 dilution.

Thirteen independent transgenic events were obtained. Southern blot analysis has confirmed the presence of the transgene in each event. Five single-gene copy events have been identified (FIG. 8).

F1 hybrid seed was produced by crossing the transgenic inbred with a suitable tester, e.g., TR7322 (available from BASF Plant Science L.L.C. d/b/a Thurston Genetics, Olivia, Minn.). AGPase activity was assayed in developing seed from the glgC3-containing transgenic events. Immature seeds were harvested at 20 days after pollination. Assays were repeated at least three times. FIG. 9 shows the results of these assays. The specific activity is expressed in FIG. 9 as µmol ADPG synthesized per minute per mg protein±standard deviation.

In comparison with the isogenic control, the transgenic events showed more than ten-fold higher AGPase activity when assayed in the presence of 3-PGA, an activator of endogenous AGPase.

EXAMPLE 6

Amino Acid Analysis of Transgenic Seed

The transgenic corn was grown and self-pollinated during the summer of 2002. Mature seed samples were ground with an IKA A11 basic analytical mill. The samples were re-ground and analyzed for complete amino acid profile (AAP) using the Association of Official Analytical Chemists (AOAC) official method 982.30 E (a, b, c), CHP 45.3.05, 2000, with four repetitions. The samples were also analyzed for crude protein (Combustion Analysis (LECO) AOAC Official Method 990.03, 2000), crude fat (Ether Extraction, AOAC Official Method 920.39 (A). 2000), and moisture (vacuum oven, AOAC Official Method 934.01, 2000).

The grain composition analysis showed that plants expressing the GlgC3 protein in the plastids of seed produce grain with enhanced nutrient content. Table 5 shows the analytical data for various transgenic inbreds grown during the summer of 2002, and Table 6 shows data for hybrid F2 grain expressing glgC3 in plastids compared to that of untransformed isogenic hybrid F2 grain (F1 was selfed during the summer of 2003).

FIGS. 10, 11 and 12 clearly demonstrate that plants over-expressing the GlgC3 protein in the amyloplast of corn seed showed a significant increase in oil and amino acid content in the grain. In comparison to wild-type grain, both inbred and F2 grain expressing the GlgC3 protein in the endosperm plastids showed at least 5% increase in oil and in several essential amino acids, including lysine, tryptophan and arginine. However, the starch content in the transgenic grain expressing the GlgC3 protein in the endosperm plastids decreased or was not changed when compared to starch content of the untransformed isogenic control grain. Transgenic grain expressing the GlgC3 protein in the cytosol of endosperm cells (EC1A1269) did not show a statistically significant increase in oil and amino acids over the isogenic control grain as the grain expressing the GlgC3 protein in the endosperm plastids (EC2A1143, EC2A1152, EC2A1224, EC2A1237, EC2A1238). These results show that the changes in nutritional content only occur when the glgC3 gene is expressed in endosperm plastids.

EXAMPLE 7

Embryo Weight Analysis of Transgenic Seed

The inbreds and F1 hybrids used in these experiments were grown and self-pollinated during the summer of 2003. The seeds were harvested at maturity. Four twenty-five kernel replicates of selfed inbred or F2 grain were used to determine the seed components. The replicates of mature seed kernels were weighed and then placed in a beaker with 50 milliliters of de-ionized water. The kernels were imbibed for 24-48 hours at 4° C. Each sample was removed from the refrigerator and separated into pericarp (including the black layer), endosperm, and embryo. The separated samples were freeze-dried for 48 hours. After 48 hours of drying, the sample dry weight was measured. In comparison to the isogenic control, the inbred and F2 grain expressing the GlgC3 protein in the plastids of endosperm has at least a 30% increase in the embryo weight relative to the whole seed weight (FIG. 13).

What is claimed is:

1. A transgenic corn seed comprising an expression construct that comprises a plant codon-optimized nucleic acid sequence that expresses an enzymatically active GlgC3 protein in endosperm plastids of said seed, wherein, when compared to an isogenic corn seed which does not express the GlgC3 protein in endosperm plastids, said transgenic corn seed is characterized by: a) an increase of at least 5% in oil content over the oil content of said isogenic corn seed; b) increases of at least about 5% in one or more of amino acids aspartic acid, glycine, isoleucine, histidine, lysine, arginine, valine, methionine, threonine, cysteine, and tryptophan over the amounts of said amino acids in said isogenic corn seed; and c) a starch content which is decreased or not changed when compared to said isogenic corn seed.

2. The transgenic corn seed of claim 1, further comprising an embryo which is at least 5% larger by weight when compared to an embryo of said isogenic corn seed.

3. The transgenic corn seed of claim 1, wherein the increase in oil content is at least 10% over the oil content of said isogenic seed.

4. The transgenic corn seed of claim 1, wherein the amino acids are lysine, tryptophan, and valine.

5. The transgenic seed of claim 1, wherein the amino acids are lysine, tryptophan, and methionine.

6. The transgenic seed of claim 1, wherein the amino acids are lysine, tryptophan, and threonine.

7. The transgenic seed of claim 1, wherein the amino acids are lysine, arginine, and cysteine.

8. The transgenic seed of claim 1, wherein the amino acids are lysine, methionine, and cysteine.

9. The transgenic seed of claim 1, wherein the amino acids are lysine, valine, and cysteine.

10. The transgenic seed of claim 1, wherein the amino acids are lysine, tryptophan, and cysteine.

11. The transgenic seed of claim 1, wherein the amino acids are lysine, tryptophan, valine and threonine.

12. The transgenic seed of claim 1, wherein the amino acids are lysine, tryptophan, valine, threonine and methionine.

13. The transgenic seed of claim 1, wherein the amino acids are lysine, tryptophan, valine, threonine, methionine and cysteine.

14. The transgenic seed of claim 1, wherein said seed is from an inbred corn line.

15. The transgenic seed of claim 1, wherein said seed is from an F1 hybrid corn plant.

16. The transgenic seed of claim 1, wherein said seed is from F2 corn grain.

17. The transgenic seed of claim 1, wherein said seed is from a corn population.

18. The transgenic seed of claim 1, wherein the enzymatically active GgC3 protein has at least tenfold higher activity when compared to the ADP-glucose pyrophosphorylase activity of the isogenic corn seed.

19. The transgenic corn seed of claim 1, wherein the increase in the one or more amino acids is at least 10% over the amino acids of said isogenic seed.

20. The transgenic corn seed of claim 1, wherein the nucleic acid sequence comprises the polynucleotide sequence of SEQ ID NO:5.

21. An expression construct adapted for expression in a plant, said construct comprising an endosperm preferred promoter, plastid transit peptide, and a nucleic acid comprising the polynucleotide of SEQ ID NO: 5.

22. A plant comprising the construct of claim 21.

23. A transgenic corn seed comprising the construct of claim 21 which encodes an enzymatically active GlgC3 protein that is expressed in endosperm plastids of said seed, wherein, when compared to an isogenic corn seed which does not express the GlgC3 protein in endosperm plastids, said transgenic corn seed is characterized by: a) an increase of at least 5% in oil content over the oil content of said isogenic corn seed; b) increases of at least about 5% in amino acids aspartic acid, glycine, isoleucine, histidine, lysine, arginine, valine, methionine, threonine, cysteine, and tryptophan over the amounts of said amino acids in said isogenic corn seed; and c) a starch content which is decreased or not changed when compared to said isogenic corn seed.

24. The transgenic corn seed of claim 23, further comprising an embryo which is at least 5% larger by weight when compared to an embryo of said isogenic corn seed.

25. The transgenic corn seed of claim 23, wherein the increase in oil content is at least 10% over the oil content of said isogenic seed.

26. The transgenic corn seed of claim 23, wherein the increase in the one or more amino acids is at least 10% over the amino acids of said isogenic seed.

27. The transgenic seed of claim 23, wherein the enzymatically active GlgC3 protein has at least tenfold higher activity when compared to the ADP-glucose pyrophosphorylase activity of the isogenic corn seed.

28. A transgenic corn seed comprising the construct of claim 21 which encodes an enzymatically active exogenous AGPase in an endosperm plastid of said seed, wherein the enzymatic activity of said AGPase is not significantly inhibited by an inhibitor of said AGPAse in the absence of an activator of said AGPase.

29. A method of producing oil- and amino acid-enriched corn seed, comprising introducing into a corn plant an expression construct comprising a plant codon-optimized nucleic acid sequence encoding a GlgC3 protein to produce transgenic corn seed expressing enzymatically active GlgC3 protein in endosperm plastids of the seed, wherein, when compared to an isogenic corn seed that does not express the GlgC3 protein in endosperm plastids, the transgenic corn seed is characterized by: a) an increase of at least 5% in oil content over the oil content of the isogenic corn seed; b) increases of at least about 5% in one or more of amino acids aspartic acid, glycine, isoleucine, histidine, lysine, arginine, valine, methionine, threonine, cysteine, and tryptophan over the amounts of said amino acids in said isogenic corn seed; and c) a starch content that is decreased or not changed when compared to the isogenic corn seed.

30. The transgenic corn seed of claim 1, wherein the amino acids are lysine, tryptophan, and arginine.

31. An animal feed comprising the transgenic corn seed of claim 1.

* * * * *

```
SEQUENCE LISTING

<160> NUMBER OF SEQ ID NOS: 9

<210> SEQ ID NO 1
<211> LENGTH: 431
<212> TYPE: PRT
<213> ORGANISM: Escherichia coli

<400> SEQUENCE: 1

Met Val Ser Leu Glu Lys Asn Asp His Leu Met Leu Ala Arg Gln Leu
 1               5                  10                  15

Pro Leu Lys Ser Val Ala Leu Ile Leu Ala Gly Gly Arg Gly Thr Arg
                20                  25                  30

Leu Lys Asp Leu Thr Asn Lys Arg Ala Lys Pro Ala Val His Phe Gly
            35                  40                  45

Gly Lys Phe Arg Ile Ile Asp Phe Ala Leu Ser Asn Cys Ile Asn Ser
        50                  55                  60

Gly Ile Arg Arg Met Gly Val Ile Thr Gln Tyr Gln Ser His Thr Leu
65                  70                  75                  80

Val Gln His Ile Gln Arg Gly Trp Ser Phe Phe Asn Glu Glu Met Asn
                85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285
```

Asp Leu Ala Ser Val Val Pro Glu Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
            325                 330                 335

Gly Cys Val Ile Ser Gly Ser Val Val Gln Ser Val Leu Phe Ser
            340                 345                 350

Arg Val Arg Val Asn Ser Phe Cys Asn Ile Asp Ser Ala Val Leu Leu
            355                 360                 365

Pro Glu Val Trp Val Gly Arg Ser Cys Arg Leu Arg Arg Cys Val Ile
    370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
            405                 410                 415

Val Thr Arg Glu Met Leu Arg Lys Leu Gly His Lys Gln Glu Arg
            420                 425                 430

<210> SEQ ID NO 2
<211> LENGTH: 1296
<212> TYPE: DNA
<213> ORGANISM: Escherichia coli

<400> SEQUENCE: 2
atggttagtt tagagaagaa cgatcactta atgttggcgc gccagctgcc attgaaatct      60
gttgccctga tactggcggg aggacgtggt acccgcctga aggatttaac caataagcga     120
gcaaaaccgg ccgtacactt cggcggtaag ttccgcatta tcgactttgc gctgtctaac     180
tgcatcaact ccgggatccg tgtatgggc gtgatcaccc agtaccagtc ccacactctg      240
gtgcagcaca ttcagcgcgg ctggtcattc ttcaatgaag aaatgaacga gtttgtcgat     300
ctgctgccag cacagcagag aatgaaaggg gaaaactggt atcgcggcac cgcagatgcg     360
gtcacccaaa acctcgacat tatccgccgt tataaagcgg aatacgtggt gatcctggcg     420
ggcgaccata tctacaagca agactactcg cgtatgctta tcgatcacgt cgaaaaaggc     480
gcacgttgca ccgttgcttg tatgccagta ccgattgaag aagcctccgc atttggcgtt     540
atggcggttg atgagaacga taaaattatc gaattcgttg aaaaacctgc taacccgccg     600
tcaatgccga acgatccgag caaatctctg gcgagtatgg gtatctacgt ctttgacgcc     660
gactatctgt atgaactgct ggaagaagac gatcgcgatg agaactccag ccacgacttt     720
ggcaaagatt tgattcccaa gatcaccgaa gccggtctgg cctatgcgca cccgttcccg     780
ctctcttgcg tacaatccga cccggatgcc gagccgtact ggcgcgatgt gggtacgctg     840
gaagcttact ggaaagcgaa cctcgatctg gcctctgtgg tgccggaact ggatatgtac     900
gatcgcaatt ggccaattcg cacctacaat gaatcattac cgccagcgaa attcgtgcag     960
gatcgctccg gtagccacgg gatgacccct aactcactgg tttccggcgg ttgtgtgatc    1020
tccggttcgg tggtggtgca gtccgttctg ttctcgcgcg ttcgcgtgaa ttcattctgc    1080
aacattgatt ccgccgtatt gttaccggaa gtatgggtag gtcgctcgtg ccgtctgcgc    1140
cgctgcgtca tcgatcgtgc ttgtgttatt ccggaaggca tggtgattgg tgaaaacgca    1200
gaggaagatg cacgtcgttt ctatcgttca gaagaaggca tcgtgctggt aacgcgcgaa    1260
atgctacgga agttagggca taaacaggag cgataa                              1296

```
<210> SEQ ID NO 3
<211> LENGTH: 431
<212> TYPE: PRT
<213> ORGANISM: Escherichia coli

<400> SEQUENCE: 3

Met Val Ser Leu Glu Lys Asn Asp His Leu Met Leu Ala Arg Gln Leu
  1               5                  10                  15

Pro Leu Lys Ser Val Ala Leu Ile Leu Ala Gly Gly Arg Gly Thr Arg
                 20                  25                  30

Leu Lys Asp Leu Thr Asn Lys Arg Ala Lys Pro Ala Val His Phe Gly
             35                  40                  45

Gly Lys Phe Arg Ile Ile Asp Phe Ala Leu Ser Asn Cys Ile Asn Ser
         50                  55                  60

Gly Ile Arg Arg Met Gly Val Ile Thr Gln Tyr Gln Ser His Thr Leu
 65                  70                  75                  80

Val Gln His Ile Gln Arg Gly Trp Ser Phe Phe Asn Glu Glu Met Asn
                 85                  90                  95

Glu Phe Val Asp Leu Leu Pro Ala Gln Gln Arg Met Lys Gly Glu Asn
                100                 105                 110

Trp Tyr Arg Gly Thr Ala Asp Ala Val Thr Gln Asn Leu Asp Ile Ile
            115                 120                 125

Arg Arg Tyr Lys Ala Glu Tyr Val Val Ile Leu Ala Gly Asp His Ile
130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Asp Lys Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Val Gln Ser Val Leu Phe Ser
            340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
370                 375                 380
```

```
Asp Arg Ala Cys Val Ile Pro Glu Gly Met Val Ile Gly Glu Asn Ala
385                 390                 395                 400

Glu Glu Asp Ala Arg Phe Tyr Arg Ser Glu Glu Gly Ile Val Leu
            405                 410                 415

Val Thr Arg Glu Met Leu Arg Lys Leu Gly His Lys Gln Glu Arg
420                 425                 430
```

<210> SEQ ID NO 4
<211> LENGTH: 1296
<212> TYPE: DNA
<213> ORGANISM: Escherichia coli

<400> SEQUENCE: 4

```
atggttagtt tagagaagaa cgatcactta atgttggcgc gccagctgcc attgaaatct    60
gttgccctga tactggcggg aggacgtggt acccgcctga aggatttaac caataagcga   120
gcaaaaccgg ccgtacactt cggcggtaag ttccgcatta tcgactttgc gctgtctaac   180
tgcatcaact ccgggatccg tcgtatgggc gtgatcaccc agtaccagtc ccacactctg   240
gtgcagcaca ttcagcgcgg ctggtcattc ttcaatgaag aaatgaacga gtttgtcgat   300
ctgctgccag cacagcagag aatgaaaggg gaaaactggt atcgcggcac cgcagatgcg   360
gtcacccaaa acctcgacat tatccgccgt tataaagcgg aatacgtggt gatcctggcg   420
ggcgaccata tctacaagca agactactcg cgtatgctta cgatcacgt cgaaaaaggc   480
gcacgttgca ccgttgcttg tatgccagta ccgattgaag aagcctccgc atttggcgtt   540
atggcggttg atgagaacga taaaattatc gaattcgttg aaaaacctgc taacccgccg   600
tcaatgccga acgatccgag caaatctctg gcgagtatgg gtatctacgt ctttgacgcc   660
gactatctgt atgaactgct ggaagaagac gatcgcgatg agaactccag ccacgacttt   720
ggcaaagatt tgattcccaa gatcaccgaa gccggtctgg cctatgcgca cccgttcccg   780
ctctcttgcg tacaatccga cccggatgcc gagccgtact ggcgcgatgt gggtacgctg   840
gaagcttact ggaaagcgaa cctcgatctg gcctctgtgg tggacaaact ggatatgtac   900
gatcgcaatt ggccaattcg cacctacaat gaatcattac cgccagcgaa attcgtgcag   960
gatcgctccg gtagccacgg gatgaccctt aactcactgg tttccggcgg ttgtgtgatc  1020
tccggttcgg tggtggtgca gtccgttctg ttctcgcgcg ttcgcgtgaa ttcattctgc  1080
aacattgatt ccgccgtatt gttaccggaa gtatgggtag gtcgctcgtg ccgtctgcgc  1140
cgctgcgtca tcgatcgtgc ttgtgttatt ccggaaggca tggtgattgg tgaaaacgca  1200
gaggaagatg cacgtcgttt ctatcgttca gaagaaggca tcgtgctggt aacgcgcgaa  1260
atgctacgga agttagggca taaacaggag cgataa                              1296
```

<210> SEQ ID NO 5
<211> LENGTH: 1299
<212> TYPE: DNA
<213> ORGANISM: Escherichia coli

<400> SEQUENCE: 5

```
atggtgagcc tggagaagaa cgaccacctg atgctggcca ggcagctgcc gctgaagagc    60
gtggccctga tcctggccgg cggcagggt accaggctga aggacctgac caacaagagg   120
gccaagccgg ccgtgcactt cggcggcaag ttcaggatca tcgacttcgc cctgagcaac   180
tgcatcaaca gcggcatcag gaggatgggc gtgatcaccc agtaccagag ccacaccctg   240
gtgcagcaca tccagagggg ctggagcttc ttcaacgagg agatgaacga gttcgtggac   300
ctgctgccgg cccagcagag gatgaagggc gagaactggt acaggggcac cgccgacgcc   360
```

-continued

```
gtgacccaga acctggacat catcaggagg tacaaggccg agtacgtggt gatcctggcc    420
ggcgaccaca tctacaagca ggactacagc aggatgctga tcgaccacgt ggagaagggc    480
gccaggtgca ccgtggcctg catgccggtc ccgatcgagg aggccagcgc cttcggcgtg    540
atggccgtgg acgagaacga caagatcatc gagttcgtgg agaagccggc caacccgccg    600
agcatgccga acgacccgag caagagcctg ccagcatgg gcatctacgt gttcgacgcc     660
gactacctgt acgagctgct ggaggaggac gacagggacg agaacagcag ccacgacttc    720
ggcaaggacc tgatcccgaa gatcaccgag gccggcctgg cctacgccca cccgttcccg    780
ctgagctgcg tgcagagcga cccggacgcc gagccgtact ggagggacgt gggcaccctg    840
gaggcctact ggaaggccaa cctggacctg ccagcgtgg tggacaagct ggacatgtac     900
gacaggaact ggccgatcag gacctacaac gagagcctgc cgccggccaa gttcgtgcag    960
gacaggagcg gcagccacgg catgaccctg aacagcctgg tgagcggcgg ctgcgtgatc   1020
agcggcagcg tggtggtgca gagcgtgctg ttcagcaggg tgagggtgaa cagcttctgc   1080
aacatcgaca gcgccgtgct gctgccggag gtgtgggtgg gcaggagctg caggctgagg   1140
aggtgcgtga tcgacagggc ctgcgtgatc ccggagggca tggtgatcgg cgagaacgcc   1200
gaggaggacg ccaggaggtt ctacaggagc gaggagggca tcgtgctggt gaccagggag   1260
atgctgagga agctgggcca caagcaggag aggtgatag                           1299
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ctctgtggtg gacaaactgg atatg                                            25
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
catatccagt ttgtccacca cagag                                            25
```

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ggaattccat atggtgagcc tggagaagaa cgac                                  34
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
tcacacagga aacagctatg ac                                                    22
```